United States Patent [19]

Horner

[11] 4,384,105

[45] * May 17, 1983

[54] POLYESTER COMPOSITIONS, SHAPED ARTICLES OBTAINED FROM THEM AND PROCESSES FOR PREPARING THEM

[75] Inventor: Patrick J. Horner, Welwyn Garden City, England

[73] Assignee: Imperial Chemical Industries PLC, London, England

[*] Notice: The portion of the term of this patent subsequent to Aug. 18, 1998, has been disclaimed.

[21] Appl. No.: 257,232

[22] Filed: Apr. 23, 1981

Related U.S. Application Data

[63] Continuation of Ser. No. 43,424, May 24, 1979, Pat. No. 4,284,756.

[30] Foreign Application Priority Data

Jun. 9, 1978 [GB] United Kingdom ............... 26606/78

[51] Int. Cl.$^3$ ......................... C08G 8/02; C08G 63/42
[52] U.S. Cl. ..................................... 528/128; 528/190
[58] Field of Search ................................ 528/128, 190

[56] References Cited

U.S. PATENT DOCUMENTS

| | | | |
|---|---|---|---|
| 3,288,755 | 11/1966 | Griehl et al. | 260/47 |
| 3,391,110 | 7/1968 | Coleman | 260/47 |
| 4,284,756 | 8/1981 | Horner | 528/128 |

FOREIGN PATENT DOCUMENTS

| | | |
|---|---|---|
| 1478252 | 4/1967 | France . |
| 43-23328 | 8/1968 | Japan . |
| 46-43992 | 12/1971 | Japan . |
| 867262 | 5/1961 | United Kingdom . |
| 924019 | 4/1963 | United Kingdom . |

*Primary Examiner*—Howard E. Schain
*Attorney, Agent, or Firm*—Cushman, Darby & Cushman

[57] ABSTRACT

UV stable linear polyesters, e.g. PET, contain in their chain copolymerized bis(hydroxyalkoxy)xanth-9-ones, preferably 3,6-bis-(2-hydroxyethoxy)xanth-9-ones. The polymers are obtained by polymerization in the presence of a tetrahydroxy benzophenone, preferably the 2,2',4,4'-isomer. The method of polymerizing in the presence of dihydric phenols to obtain ethoxyaryloxy polyesters is also described.

4 Claims, 1 Drawing Figure

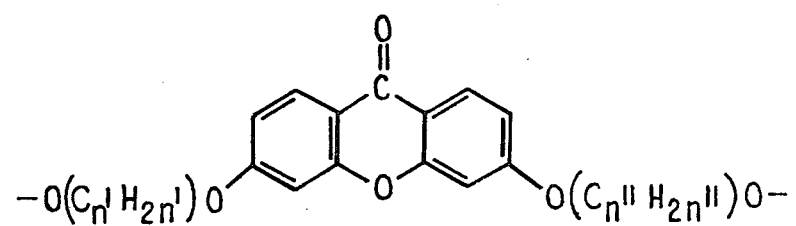
FORMULA 1

POLYESTER COMPOSITIONS, SHAPED ARTICLES OBTAINED FROM THEM AND PROCESSES FOR PREPARING THEM

This is a continuation, of application Ser. No. 43,424 filed May 24, 1979 now U.S. Pat. No. 4,284,756.

Linear polyesters have only poor stability under the influence of UV irradition. It is an object of this invention to improve the UV stability of linear polyesters.

Linear polyesters are well known thermoplastic polymers which have chains consisting of alternating residues of glycols and dicarboxylic acids, the residues being connected by means of ester linkages. Many acids and glycols have been proposed for the preparation of linear polyesters. The acids include (a) terephthalic acid, (b) isophthalic acid, (c) naphthalene-2,6-dicarboxylic acid, and (d) bis(carboxyphenoxy)ethane. The glycols include alkane diols with 2 to 10 carbon atoms (e.g. ethylene glycol and 1,4-butane-diol), and 1,4-dimethylol cyclohexane. By far the commonest polyester is poly(ethylene terephthalate). Other commercially used linear polyesters include (a) a copolymer of ethylene glycol with a mixture of terephthalic acid and isophthalic acid said mixture containing 80 to 95 mole % of the terephthalic acid, (b) a polymer of 1,4-butanediol and terephthalic acid, and (c) homopolymer of terephthalic acid and 1,4-dimethylolcyclohexane.

According to this invention a linear polyester contains in its molecule residues of bis(hydroxyalkoxy)xanth-9-ones, the amount of the said bis(hydroxyalkoxy)xanth-9-ones being 0.05 to 10% by weight, preferably 0.05 to 5% by weight, based on the total polymer.

For example such a linear polyester has an IV above 0.50 and it contains in its molecule residues of:
(A) Dicarboxylic acids selected from
 (i) terephthalic acid
 (ii) isophthalic acid
 (iii) naphthalene-2,6-dicarboxylic acid
 (iv) bis(carboxyphenoxy)ethane;
(B) Glycols with 2 to 10 carbon atoms in the molecule, e.g. ethylene glycol, 1,4-butane diol and 1,4-dimethylolcyclohexane; and
(C) bis(hydroxyalkoxy)xanth-9-ones; the amount of (C) being between 0.05 and 10% by weight, preferably 0.05 and 5% by weight based on the amount of (A)+(B)+(C).

An important class of linear polyesters according to the invention have as repeating unit:

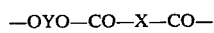

wherein at least 80 mole% of the X groups represent p-phenylene and the remainder represent m-phenylene and at least 90% of the Y groups represent $-C_nH_{2n}-$ where n is an integer from 2 to 10, e.g. $-CH_2-CH_2-$ and at least 0.1% of the Y groups represent residues of 3,6-bis(hydroxyalkoxy)xanth-9-ones said residues having the formula 1 where n' and n" are integers from 1 to 10, e.g. n'=n"=2.

(Formula 1 is given in the accompanying drawing.)

The invention includes polyesters as described above which also contain in their molecule 0.05 to 10% by weight, preferably 0.05 to 5% by weight of residues of 2,4-dihydroxy benzoic acid. Preferably the mole ratio of xanthone to benzoic acid residues is 1:1 to 1:07.

Linear polyesters are obtained by a two-stage process. A precursor is obtained in the first stage. This precursor is a low molecular weight ester of the glycol and the dicarboxylic acid. In the second stage the precursor is subjected to polycondensation to increase its molecular weight and thereby obtain the polyester.

There are two common methods for preparing the precursor. In the ester interchange method the glycol is reacted with a dialkyl ester of the dicarboxylic acid. A low molecular weight alcohol is removed thus forming the glycol ester by ester interchange. For example ethylene glycol is reacted with dimethyl terephthalate to form ethylene glycol terephthalate and methyl alcohol (which is removed by distillation). The rate of reaction can be increased by incorporating ester interchange catalysts in the reaction mixture. Suitable ester interchange catalysts include zinc acetate, manganese acetate, calcium acetate, cobalt acetate and titanium tetraisopropoxide.

In the direct esterification method the glycol and the acid are esterified to form the glycol ester with the removal of water, e.g. ethylene glycol is esterified with terephthalic acid. It is usual to carry out direct esterification without catalysts. However, under the acidic conditions which apply during direct esterification, ethylene glycol tends to dimerise according to the reaction:

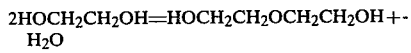

Some of the diethylene glycol produced by this reaction gets incorporated into the polymer chain but small amounts cause no adverse effects except a lowering of the softening point. The formation of diethylene glycol can be reduced, and hence the softening point kept at a satisfactory level, by including an alkaline compound, e.g. sodium hydroxide, in the direct esterification reaction mixture.

The second stage is carried out by heating the precursor at a temperature above its melting point under low pressure, e.g. below 5 mbar, with stirring. During polycondensation glycol is eliminated (and removed by distillation). As the reaction proceeds the molecular weight and viscosity increase. The increase in viscosity can be used to ascertain when the desired molecular weight has been achieved.

Polycondensation catalysts are usually incorporated during the polycondensation. Suitable polycondensation catalysts include antimony trioxide, germanium dioxide, mixtures of these two, titanium alkoxides, lead oxides and zinc. Some catalysts, e.g. germanium dioxide, are conveniently dissolved in alkali before they are added to the reaction system. In such cases it is particularly appropriate to utilise the alkali which is present in the direct esterification stage to dissolve the catalyst (even though the catalyst has no effect upon the direct esterification).

The metals present during stage 1 remain in the polymer and, when colourless products are needed, it is necessary to avoid the residues being in the form of coloured derivatives. An acid of phosphorus or an ester of such an acid can be added to the polycondensation mixture; these compounds reduce the colour caused by the metals. Specific examples of phosphorus compounds suitable for adding to the polycondensation reaction include phosphoric acid, triphenyl phosphates and phosphorous acid.

This invention includes three methods of making polyesters. These methods will now be described.

METHOD 1

According to Method 1 linear polyesters, especially polyethylene terephthalate, are prepared by polycondensation in the presence of 0.04% to 10% by weight, preferably 0.04 to 5% by weight, based on the total reactants of a dihydric phenol heat stable at 250° C.

It is well known that phenols are difficult to esterify with carboxylic acids and therefore phenols cannot readily be incorporated into the chain of a polyester by this method. We have found that when a dihydric phenol is included in a polycondensation mixture a most unexpected reaction occurs. Each hydroxyl group of the phenol reacts with (combined or uncombined) glycol present in the system to form an ether linkage thereby converting the phenol to a hydroxyalkoxy derivative. This derivative forms ester linkages with acid residues in the precursor. The overall reaction can be represented as follows (where HOOCACOOH represents the dicarboxylic acid; HOGOH represents the glycol and HOXOH represents the phenol)

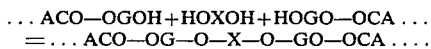
... ACO—OGOH+HOXOH+HOGO—OCA ...
= ... ACO—OG—O—X—O—GO—OCA ....

We have no evidence of the mechanism whereby the reaction occurs but we are able to demonstrate the overall effect because:

(a) the phenol cannot be extracted or detected in the polyester, (b) if the polyester is hydrolysed to its acid and glycol the hydroxyalkoxy derivative of the phenol is present in the hydrolysate, (c) the spectrographic results are compatible with the structure proposed for the product of the reaction.

The following are examples of dihydric phenols suitable for use in the reaction. The phenols are classified by parent ring systems.

XANTHONE 3,6-dihydroxyxanthone.

ANTHRANQUINONE 2,6; 1,4 and 1,8-dihydroxanthraquinone.

BENZOPHENONE 4,4'-dihydroxybenzophenone.

FLAVONE 6,7-dihydroxyflavone.

ACETOPHENONE 2,4-dihydroxyacetophenone.

METHOD 2

According to Method 2 linear polyesters containing xanth-9-one residues (i.e. polyesters as described above) are prepared by polycondensation in the presence of 0.04 to 10% by weight, preferably 0.04 to 5% by weight, based on the total reactants, of 2,2',4,4'-tetrahydroxybenzophenone. It is well known that 2,2',4,4'-tetrahydroxybenzophenone readily dehydrates to 3,6-dihydroxyxanth-9-one. It is believed that this dehydration occurs under the conditions of polycondensation and the product reacts as in method 1.

METHOD 3

According to Method 3 linear polyesters containing xanth-9-one residues (i.e. polyesters as described above) are prepared by incorporating a bis(hydroxyalkoxy)xanth-9-one preferably the 3,6 isomer, in either the precursor or, into the ingredients from which the precursor is prepared. The preferred alkoxy group is ethoxy.

Method 2 is particularly suitable for polyesters based on glycols other than ethylene glycol, e.g. polybutyleneterephthalate.

The polyesters according to the invention can be converted to shaped articles which have good stability to UV irradiation. The shaped articles include fibre and films, e.g. metallised film and coextruded laminates which have the polymer according to the invention as one or both outer layers. The metallised films may be used as reflectors in solar energy collectors. The transparent films may be used as windows, greenhouses, cloches, transparent coverings for solar cells.

The shaped articles may be made entirely from the polyesters according to the invention or they may be made from blends of this polymer and conventional polyesters.

The preparation of a polymer according to the invention will now be described by way of example.

In the Examples 2,2',4,4'-tetrahydroxybenzophenone will be abbreviated to THBP.

EXAMPLE 1

This Example describes the preparation of a linear polyester according to the invention using a two-stage process comprising (1) direct esterification followed by (2) polycondensation. To start Stage 1, the following reactants were charged to an autoclave:

60.5 kg: terephthalic acid
30 liters: ethylene glycol
3.5 g: germanium dioxide
3.5 g: sodium hydroxide (For convenience of handling the GeO$_2$ and the NaOH were both dissolved in the same small portion, about 50 g, of the ethylene glycol.

The autoclave was pressurised to about 3 atm and heated with stirring. The reaction commenced and water of esterification was removed with some of the excess of glycol. The temperature remained at the reflux temperature. All the water of esterification had been removed in about 2.5 hours when the temperature had risen to 248° C. The pressure was released over a period of about 5 minutes and a small amount (about 5 liters) of glycol removed. This completed the (conventional) direct esterification and 119 g of triphenylphosphate (in methanol) were added. 77 kg of product, which was a conventional precursor for the preparation of polyethylene terephthalate, were obtained and used for polycondensation.

The precursor was then transferred to the polycondensation vessel and prepared for Stage 2, i.e. polycondensation, by the addition of 2100 g THBP, i.e. 2.7% by weight of the precursor, and 21 g of antimony trioxide. Removal of glycol was started by distillation at 230° C. under atmospheric pressure with stirring. When the distillation had started, the pressure was slowly reduced to 0.3 m bar and the temperature was kept at 290° C. The pressure was allowed to return to atmospheric, the polymer was removed from the polycondensation vessel and cut into chip. The total weight of the polymer was 61 kgs.

It is emphasized that the preparation described in Example 1 is conventional except for the addition of THBP. The polymer was film-forming quality poly(ethylene terephthalate) having an IV of 0.6 and a softening point of 254°. It contained about 3% by weight of residues of 3,6-bis(2-hydroxyethoxy)xanth-9-one, i.e. residues of Formula 1 where $n'=n''=2$.

EXAMPLE 2

The polymer from Example 1 was used to prepare film according to the invention. The chip from Example 1 was blended in the weight ratio 1:3 with conventional poly(ethylene terephthalate). Thus the blend, which was converted to biaxially oriented film 125 um thick, contained 0.75% of the xanthone residues. Properties of this film are given in Table 1 below.

EXAMPLE 3

The chip from Example 1 was blended in weight ratio 1:2 with the same conventional poly(ethylene terephthalate) used in Example 2. The blend, which contained 1% of the xanthone residues, was converted to biaxially oriented film 125 um thick. Properties of this film are given in Table 1 below.

TABLE 1

|  |  | EXAMPLE | | | |
|---|---|---|---|---|---|
|  |  | 2 | | 3 | |
|  |  | MD | TD | MD | TD |
| Yield | kg/cm² | 1120 | 1100 | 1440 | 1120 |
| Ultimate Tensile Strain | kg/cm² | 2200 | 2100 | 2250 | 2150 |
| Elongation to Break | % | 117 | 123 | 128 | 129 |
| Modulus | tonnes/cm² | 50.3 | 40.0 | 44.6 | 41.5 |
| Amount Xanthone | % wt | 0.75 | | 1.00 | |

As is illustrated by the results quoted in Table 1 both films were of good quality with satisfactory mechanical properties. The stability of the films to UV irradiation was substantially better than conventional poly(ethylene terephthalate).

Analysis of the chip of Example 1 and the films of Examples 2 and 3 showed:
(a) there was no detectable THBP in the polymer or film,
(b) after hydrolysis of polymer and film to terephthalic acid and ethylene glycol, there was no detectable THBP in the hydrolysate,
(c) the hydrolysate contained 3,6-bis(2-hydroxyethoxy)xanth-9-one (which is a new compound) but this compound could not be extracted from the polymer or film.
(d) The hydrolysate also contained residues of 2,4-dihydroxybenzoic acid.

EXAMPLE 4

This Example describes the preparation of a linear polyester according to the invention using a two-stage process comprising (1) direct esterification followed by (2) polycondensation. To start Stage 1, the following reactants were charged to an autoclave:

60.5 kg: terephthalic acid
30 liters: ethylene glycol
0.7 kg: 3,6-dihydroxyxanth-9-one
3.5 g: germanium dioxide
3.5 g: sodium hydroxide
(For convenience of handling the GeO₂ and the NaOH were both dissolved in the same small portion, about 50 g, of the ethylene glycol.)

The autoclave was pressurised to about 3 atm and heated with stirring. The reaction commenced and water of esterification was removed with some of the excess of glycol. The temperature remained at the reflux temperature. All the water of esterification had been removed in about 2½ hours when the temperature had risen to 248° C. The pressure was released over a period of about 5 minutes and a small amount (about 5 liters) of glycol removed. This completed the direct esterification and 119 g of triphenylphosphate (in methanol) were added. 77 kg of product, which was a conventional precursor for the preparation of polyethylene terephthalate, were obtained and used for polycondensation. The precursor was then transferred to the polycondensation vessel and prepared for Stage 2, by the addition of 21 g of antimony trioxide. Removal of glycol was started by distillation at 230° C. under atmospheric pressure with stirring. When the distillation had started the pressure was slowly reduced to 0.3 m bar and the temperature was kept at 290° C. The pressure was allowed to return to atmospheric, the polymer was removed from the polycondensation vessel and cut into chip. The total weight of the polymer was 61 kg.

It is emphasized that the preparation described in Example 4 is also conventional except for the addition of the 3,6-dihyroxyxanth-9-one. The polymer was film-forming quality poly(ethylene terephthalate) having an IV of 0.6 and a softening point of 254°. It contained about 1% by weight of residues of 3,6-bis(2-hydroxyethoxy)xanth-9-one, i.e. residues of Formula 1 where $n'=n''=2$. Film was prepared for the polymer which had the same film forming properties as the polymer of Example 1 but its UV stability was even better than that of Example 1. (Note. The 3,6-dihydroxyxanth-9-one is sparingly soluble in the precursor and it is, therefore, more convenient to add it at the start of stage 1.)

Analysis of the polymer of Example 4 and the films made from it showed:
(a) there was no detectable 3,6-dihydroxyxanth-9-one,
(b) after hydrolysis of polymer and film to terephthalic acid and ethylene glycol, there was no detectable 3,6-dihydroxyxanth-9-one in the hydrolysate,
(c) the hydrolysate contained 3,6-bis(2-hydroxyethoxy)xanth-9-one (which is a new compound) but this compound could not be extracted from the polymer or film,
(d) the hydrolysate contained no detectable 2,4-dihydroxybenzoic acid.

EXAMPLE 5

The method of Example 1 was repeated with a wide range of phenols to illustrate its general applicability.

Precursor was prepared as described in stage 1 of Example 1 and divided into aliquots, each of mass 100 g. One of the dihydric phenols named in Table 2 was added to each aliquot and the resulting mixture subjected to polycondensation as specified in stage 2 of Example 1.

TABLE 2

1,4-dihydroxyanthraquinone
1,8-dihydroxyanthraquinone
4,4'-dihydroxybenzophenone
4,4'-dihydroxydiphenyl sulphone
2,4-dihydroxyacetophenone
6,2-dihydroxyflavone
2,2-bis(4-hydroxyphenyl)propane
Methylene-bis-2,4-dihydroxybenzophenone.

The polycondensations were carried out with each of the phenols named in Table 2. In one case 2 g, in the other case 10 g, of the phenol were added to the 100 g of precursor before polycondensation.

Good polyesters were obtained in all cases and NMR and IR spectroscopy proved that the phenols had been ethoxylated and copolymerised.

Examples 6 and 7 illustrate the use of 3,6-bis(hydroxyethoxy)xanth-9-one to prepare polyesters. The 3,6-bis(hydroxyethoxy)xanth-9-one was prepared from the following ingredients.
28.2 g: 3,6-dihydroxyxanthone
17.2 g: sodium hydroxide
33.0 g: 2-bromoethanol
150 ml: distilled water The sodium hydroxide was dissolved in the distilled water and the xanthone was dissolved in the alkaline solution. This gave a dark red solution which was filtered into a 500 ml round bottom flask equipped with stirrer, heater, reflux condenser, thermocouple pocket and a dropping funnel. The bromoethanol was placed in the alkaline solution and the temperature of the mixture was raised gradually. At 64° C. a precipitate began to form and the temperature was maintained between 60° C. and 64° C. for 4 hours.

The contents were removed from the flask and the precipitate was separated by filtration. When dry 6.2 g of a creamy white solid were obtained. NMR showed that this solid was 3,6-bis(2-hydroxyethoxy)xanth-9-one about 99.5% pure.

The liquor was further reacted with chloroethanol. A further 16.7 g of 3,6-bis(2-hydroxyethoxy)xanth-9-one was obtained the purity of this sample was about 95%.

(Although 3,6-dihydroxyxanthone is a known compound that used in the Example was prepared as follows. A large sample of 2,2',4,4'-tetrahydroxybenzophenone was placed in an air oven at 180° C. and left overnight. In the morning it had undergone ring closure to 3,6-dihydroxyxanthone.)

EXAMPLE 6

Residues of 3,6-bis(hydroxyethoxy)xanth-9-one were incorporated into poly(butyleneterephthalate) using a two stage method wherein stage 1 comprised ester interchange between 1,4-butane diol and dimethyl terephthalate and stage 2 comprised polycondensation of the precursor of stage 1 in the presence of 3,6-bis(hydroxyethoxy)xanth-9-one.

To carry out stage 1 the following were charged to the ester interchange vessel:
640 g dimethylterephthalate
593 g 1,4-butanediol
0.1 g titanium tetraisopropoxide.

(The third ingredient, the transesterification catalyst, was added as 1% solution in butanol.)

The reaction mixture was initially heated at 156° C. and the heating continued until 267 mls of methanol had been collected when the temperature of the reaction mixture had risen to 218° C. The reaction mixture was allowed to cool to 170° C. when it was poured into a tray where it solidified at room temperature. It cooled to a white solid which was the precursor for stage 2.

To carry out stage 2 (polycondensation) the following reactants were used:
100 g Precursor (from stage 1)
2.0 g 3,6-bis(hydroxyethoxy)xanth-9-one
0.6 g titanium tetraisopropoxide.

The polycondensation mixture was heated at 245° C. under 0.4 mm Hg until a suitable melt viscosity had been achieved.

The product was poly(tetramethylene terephthalate) which contained residues of the 3,6-bis(hydroxyethoxy)xanth-9-one. It had excellent UV stability.

EXAMPLE 7

The method of Example 1 was repeated adding 700 g of 3,6-bis(hydroxyethoxy)xanth-9-one to the polycondensation mixture instead of 2100 g THBP.

The resultant polyester contained about 1% by weight of 3,6-bis(2-hydroxyethoxy)xanth-9-one residues and it was substantially the same as that of Example 1. It more closely resembled the product of Example 4 in that it had very good UV stability and there appeared to be no residues of 2,4-dihydroxybenzoic acid in the polymer.

EXAMPLE 8

The method of Example 1 was repeated using 2,6-naphthalene-dicarboxylic acid instead of terephthalic acid.

EXAMPLE 9

A precursor was obtained by transesterifying the following ingredients:
70 kg dimethylester of bis(carboxyphenoxy)ethane
35 liter ethylene glycol
30 g manganese acetate (catalyst)

1400 g of THBP and 35 g antimony oxide were added to the precursor and the mixture subjected to polycondensation as described in Example 1.

The polyester of Examples 8 and 9 had good properties, including good UV stability. The results showed that the THBP was converted into 3,6-bis(hydroxyethoxy)xanth-9-one residues which were incorporated in the polyester chain.

I claim:

1. A shaped article formed of a linear polyester which contains in its molecule polymerised residues of bis(hydroxyalkoxy)xanth-9-ones of the formula

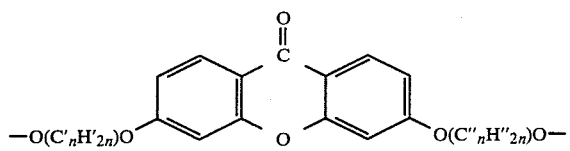

wherein
n' = 1 to 10 and
n" = 1 to 10,
the amount of said polymerised residues being 0.05 to 10 percent based on the total polymer.

2. A shaped article according to claim 1 wherein the linear polyester has as repeating units:

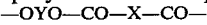

wherein
at least 80 mole % of the X-groups represent p-phenylene and the remainder represent m-phenylene
at least 90% of the Y groups represent $C_2H_4$ and at least 0.1% of the Y groups represent polymerised units of 3,6-bis(hydroxyethoxy)xanth-9-one.

3. A shaped article according to claim 2 which is in the form of a biaxially oriented film.

4. A shaped article according to claim 1 which is in the form of a film.